United States Patent [19]
Friedman et al.

[11] Patent Number: 6,004,566
[45] Date of Patent: Dec. 21, 1999

[54] TOPICAL AND TRANSDERMAL DELIVERY SYSTEM UTILIZING SUBMICRON OIL SPHERES

[75] Inventors: Doron Friedman, Carmei Yossef; Joseph Schwartz; Haim Aviv, both of Rehovot, all of Israel

[73] Assignee: Pharmos Corp., New York, N.Y.

[21] Appl. No.: 08/036,116

[22] Filed: Mar. 23, 1993

[30] Foreign Application Priority Data

Mar. 26, 1992 [IL] Israel ........................................ 101387

[51] Int. Cl.⁶ .................................................. A61K 9/107
[52] U.S. Cl. ........................ 424/400; 424/401; 424/450; 424/448; 424/449; 514/78; 514/786; 514/817; 514/846; 514/859; 514/863; 514/886; 514/887; 514/938; 514/943
[58] Field of Search ...................................... 424/400, 401, 424/450, 448, 449; 514/78, 772.5, 786, 816, 817, 818, 844, 846–847, 858–865, 886, 887, 936–939, 943, 946

[56] References Cited

U.S. PATENT DOCUMENTS

| 4,529,601 | 7/1985 | Broberg et al. ........................... 514/626 |
| 4,613,330 | 9/1986 | Michelson ................................. 504/890 |
| 4,647,586 | 3/1987 | Mizushima et al. ...................... 514/532 |
| 4,963,367 | 10/1990 | Ecanow .................................... 424/485 |

FOREIGN PATENT DOCUMENTS

| 0 014 509 | 8/1980 | European Pat. Off. . |
| 0 063 870 | 11/1981 | European Pat. Off. . |
| 0 315 079 | 5/1989 | European Pat. Off. . |
| 0 433 132 | 6/1991 | European Pat. Off. . |
| 0 480 690 | 4/1992 | European Pat. Off. . |
| 0 506 197 | 9/1992 | European Pat. Off. . |
| 2 113 568 | 8/1983 | United Kingdom . |

OTHER PUBLICATIONS

L.C. Collins–Gold et al., "Parental Emulsions for Drug Delivery", Advanced Drug Delivery Reviews, 5:189–208 (19990).

R.J. Frankerd et al., "The Use of Oil–In–Water Emulsions as a Vehicle for Parental Drug Administration", Journal of Parental Science and Technology, 44 No. 3:139–149 (1990).

Primary Examiner—Jyothsna Venkat
Attorney, Agent, or Firm—Pennie & Edmonds LLP

[57] ABSTRACT

The present invention relates to a delivery system which includes a bioactive drug or cosmetic substance presented in the form of submicron oil spheres alone, or drugs or cosmetic substances in a combination with the oil spheres in an aqueous suspension or emulsion. Optionally, a skin penetration enhancer may be included in such formulations. Such preparations achieve improved bioavailability and exert larger pharmacological effects than an equivalent dose of the drug or cosmetic formulated in conventional creams, lotions or oleaginous bases.

17 Claims, 3 Drawing Sheets

TOPICAL AND TRANSDERMAL DELIVERY SYSTEM UTILIZING SUBMICRON OIL SPHERES

FIELD OF THE INVENTION

The present invention relates to the field of drug delivery and, particularly, to the administration of various pharmaceutical or cosmetic agents to a patient through the skin or mucous membranes by the application of innovative, non-irritating topical compositions of these agents in the form of submicron oil spheres.

BACKGROUND OF THE PRESENT INVENTION

The delivery of drugs to the skin and systemically via the skin is hampered by the natural barrier of the stratum corneum. Creams and lotions are classical vehicles for delivering drugs and cosmetics to the skin. These preparations are semi-solid, bi-phasic preparations where oil spheres are dispersed in water. The droplet size of these spheres has not been a concern in conventional pharmaceutically marketed semi-solid creams and lotions. Most commercially marketed medical creams include oil spheres having a size of 5 to 50 microns. For example, VOLTAREN EMULGEL has a droplet size above five microns, as confirmed both microscopically and with photon correlation spectroscopy (Coulter N4MD).

Moreover, the scientific literature does not address the droplet size of the internal oily phase of topically applied emulsions. On the few occasions that refer to topical cream or lotion dosage forms, the indicated droplet size is in the range of a few to tens of microns. For example, U.S. Pat. No. 4,529,601 relates to an eutectic mixture of lidocaine and tetracaine which allegedly produces a good local anesthetic effect that may not be achieved otherwise.

EP 00 63 870 claims good anti-inflammatory activity and high safety of an anti-inflammatory substance in combination with MCT oil and carboxy vinyl polymer. Again, droplet size is not emphasized.

EP 04 33 132 discloses the topical cosmetic application of vesicles for incorporation of essential oils. It is also possible, according to that patent application, that small droplets of various sizes of the essential oils may be formed.

The cases cited above exemplify numerous patents concerning topical uses of classical macroemulsions, in which the oily droplets are generally well above one micron in diameter. There is also a vast body of prior art utilizing liposome preparations for enhanced dermal penetration of pharmaceuticals (Egbaria & Weiner, Adv. Drug Delivery Rev. 5, 287 (1990)). However, there are inherent problems in formulating stable liposomes, since these structures are lipid bilayers enveloping an aqueous phase. Another type of drug carrier, distinct from both classical emulsions and liposomes are the microemulsions which are usually thermodynamically stable, transparent and have particles consistently below 200 nm (Rosano, H. L., Carallo, J. L. and Lyons, G. B. Microemulsion Systems, Vol. 24, Chap. 16, H. L. Rosano and M. Clause eds. Marcel Dekker, Inc., New York (1987), pp. 271). However, microemulsions contain a large proportion of surfactant to lipid and therefore are inappropriate for dermal applications due to anticipated problems of irritancy.

EP 05 06 197 discloses an aqueous suspension of nanoparticles of at least one lipid and an emulsifier, wherein the nanoparticles have a size of between 50 and 1000 nm. The lipids used therein, however, are either a solid lipid or a mixture of solid lipids.

In the field of topical and transdermal medication and delivery of drugs, much effort has been invested in providing chemical enhancers of drug penetration, such as DMSO and azones. Many of these substances cause irritation and are not desirable due to their toxicity. There remains a need, therefore, for a method and vehicle which will enable or facilitate efficient transport of poorly soluble drugs through the skin for topical or transdermal use, when provided as an aqueous dispersion of same.

SUMMARY OF THE INVENTION

This invention relates to a composition for topical application of pharmaceuticals or cosmetics comprising submicron size droplets of a drug with oily excipients either alone or dispersed in an aqueous medium. The droplet size is below one micron, and preferably in the range of about 0.05 to 0.5 microns. A semi-solid state is advantageous for the practical application of the dosage form on the skin when used as a cream.

Specifically, the submicron size droplets include about 0.5 to 30% of a first component comprising an oily liquid, about 0.1 to 10% of a second component of an emulsifier and about 0.05 to 5% of a non-ionic surfactant. These droplets are suspended in an aqueous component which forms the continuous phase of an emulsion. The composition provides enhanced topical and/or transdermal systemic effects compared to similar compositions which have larger size droplets. A mean droplet size in the range of between about 0.1 and 0.3 µm is preferred.

The first component is typically present in an amount of about 5 to 20%, and includes oily liquids such as a medium chain triglyceride oil having a chain length of about 8 to 12 carbons, a vegetable oil, a mineral oil, an oil of animal source, a synthetic derivative thereof, or mixtures thereof. To form a viscous composition, the oily liquid may be present in an amount of about 20 to 30%. Alternatively, one or more adjuvants such as gelling agents or thickening agents may be included to increase the viscosity of the composition and form a cream.

The emulsifier may be a phospholipid compound or a mixture of phospholipids, such as lecithin, phosphatidylcholine, phosphatidylethanolamine or mixtures thereof, in an amount of about 0.2 to 5%. The surfactant may be a non-ionic alkylene oxide condensate of an organic compound which contains one or more hydroxyl groups, such as an ethoxylated alcohol or ester compound, in an amount of about 0.2 to 5%.

The first component may comprise an active ingredient in any one of a number of forms. For simplicity, the active ingredient may be in the form of an essentially water-insoluble oily liquid, such that other oily liquids are either not needed or can be mixed therewith. Instead, the active ingredient can be present as a solid, essentially water-insoluble or slightly water-soluble substance which is partially or fully dissolved or dispersed in one of the oily liquids mentioned above. For such mixtures or dispersions, the active ingredient may be present in an amount of 0.05 to 2.5%.

The active ingredient may be one or more of the following: a steroid, non-steroidal anti-inflammatory drug, antibiotic, tranquilizer, sedative, anti-histaminic, antifungal, antibacterial, antiviral, disinfectant, antipsoriasis agent or a local anesthetic. Specifically, the active ingredient is clotrimazole, bifonazole, tetracycline, miconazole, triamcinolone, amphotericin B, gentamicin, hydrocortisone, iodoxuridine, diphenhydramine, minoxidil, lidocaine, tetracaine and clindamycin.

The composition may also include a dispersion enhancer in an amount sufficient to promote the homogeneity of the composition, or a viscosity enhancing agent in an amount sufficient to impart a semi-solid form to the composition. A preferred viscosity enhancing agent is a physiologically acceptable high molecular weight compound. In addition, a skin penetration enhancer may be added in an amount sufficient to enhance the penetration of the composition through skin after the composition is topically applied thereto.

The invention also relates to a method for obtaining enhanced topical and/or transdermal systemic effects which comprises formulating one of the compositions described above and topically applying the composition to the skin of a subject, wherein the composition provides enhanced topical and/or transdermal systemic effects compared to the same compositions which have larger size droplets. In this method, the active ingredient may be a barbiturate, benzodiazepine, ketotifen, phenytoin, phenothiazines, cyclosporin, diphenoxylate, diclofenac, dexamethasone, prostaglandin, nifedipine, nitroglycerine, atropine, verapamil, fentanyl, lipophilic peptide or miconazole.

When the method is used to treat a skin condition, the active ingredient may be Vitamin A, Vitamin E, a retinoid, a carotene or benzoyl peroxide, and is applied to alleviate, reduce or prevent dermatological conditions and diseases, including atopic dermatitis, psoriasis, acne and other types of skin inflammations or viral, fungal or bacterial skin infections.

The invention also relates to a method for reducing local irritation produced by pharmaceuticals which induce local inflammatory reactions by topically applying one of the compositions described above. Depending upon the selection of the active ingredient, the method may be used for achieving local anesthesia or analgesia, or for providing general analgesia.

Also, an article, such as an occlusive dressing or adhesive patch, can be used to administer active ingredients such as a steroid, nicotine, nitroglycerine or the like.

BRIEF DESCRIPTION OF THE DRAWINGS

In the following detailed description, reference will be made to the annexed drawings, in which.

DETAILED DESCRIPTION OF THE INVENTION

According to the present invention, pharmaceutical and cosmetic compositions are provided in the form of submicron droplets of water-insoluble liquid drugs or cosmetically active substances alone, or drugs or cosmetically active substances with oily excipients and/or solvents in an aqueous medium. These compositions promote percutaneous penetration on topical application and local or transdermal effects. Advantageously, a chemical entity which acts as a skin penetration enhancer may be added to the above for enhancing activity. Thus, the overall pharmacological effect, while using such a chemical enhancer in conjunction with such submicron oil spheres, will be greater than either one of them alone.

In contrast to the prior art, the present invention relates to oily spheres having an average diameter in the submicron range, which are both physically and chemically distinct from the known art of liposome-type lipid vesicles and from the known art of microemulsions in which surfactants or synthetic emulsifiers comprise a large proportion of the composition. In terms of chemical composition, the particles are somewhat similar to classical emulsions, but due to the finely divided particulate nature of the current invention, a significantly enhanced dermal penetration is achieved. We have thus termed these droplets as submicron emulsion oil spheres.

Insoluble drugs or cosmetically active substances may be dispersed in an aqueous medium as solid or liquid particles to form a suspension. One aspect of this invention relates to drugs or cosmetically active substances that are liquid at room temperature and may be dispersed as liquid, water-insoluble droplets with the desired droplet size range. Otherwise, for drugs or cosmetics which are solid at room temperature and in the shape of powder or crystals, mixtures with an oil are a preliminary required step in order to obtain oily droplets in aqueous suspension.

An emulsion is a dispersion of oil in water ("o/w"), and can be defined as either a macroemulsion or a microemulsion. A macroemulsion is a cloudy turbid composition having an oil-droplet size of 0.5 to 100 $\mu$m and is generally thermodynamically unstable. In comparison, a microemulsion is a translucent to transparent composition having a droplet size of 0.005 to 0.5 $\mu$m, is thermodynamically stable and is generally self emulsifying. See, e.g., Friberg et al. (1987) Microemulsions Structure and Dynamics, CRC Press Inc., Boca Raton, Fla., pp. 154. Also, the proportion of surfactants to oil required to generate microemulsions is generally much higher than in macroemulsions.

The term "submicron" is used herein to mean a size of about 0.05 to 0.5 $\mu$m, and preferably about 0.1 to 0.3 $\mu$m. Thus, submicron droplets of these sizes would be smaller than those of a classical macroemulsion, which has droplet sizes of above about 0.5 $\mu$m, but generally larger than those of a classical microemulsion, which, for practical purposes, has droplet sizes of less than about 0.1 $\mu$m.

These submicron droplets can easily be sterilized by filtration, for example, in 0.45 $\mu$m and/or 0.22 $\mu$m filters, are more stable in long-term storage and can better withstand sterilization in an autoclave.

An oil-in-water emulsion is a dispersion of droplets or colloidal particles in an aqueous medium, with the colloid particles having an oily core surrounded by an interfacial film of the emulsifiers and surface acting agents or surfactants. For clarity in understanding the present invention, the following terms will be used:

"aqueous phase"—to denote the aqueous solution in which the droplets or colloid particles are dispersed;

"oily phase"—to denote the oily cores of the droplets or colloidal particles; and "amphiphilic phase"—to denote the interfacial films of emulsifier and surfactant surrounding the oily phase of the droplets or colloidal particles.

In this invention, the oil may be a vegetable oil, a mineral oil, a medium chain triglyceride (MCT) oil, i.e., a triglyceride oil in which the carbohydrate chain has 8–12 carbons, or a combination of two or three of such oils. Although MCT oil can be considered as a component of vegetable oil, it is separately identified herein because of its particular utility as a preferred oil for use in the present droplets. In addition, MCT oil is available commercially. Examples of such MCT oils include TCR (trade name of Societe Industrielle des Oleagineaux, France for a mixture of triglycerides wherein about 95% of the fatty acid chains have 8 or 10 carbons) and MIGLYOL 810 or 812 (trade name of Dynamit Nobel, Sweden for a mixed triester of glycerine and of caprylic and capric acids). Examples of vegetable oils include soybean oil, cotton seed oil, olive oil, sesame oil and castor oil. The mineral oils may be natural hydrocarbons or their synthetic analogs. Oily fatty acids, such as oleic acid and linoleic acid, fatty alcohols, such as oleyl alcohol, and fatty esters, such as sorbitan monooleate and sucrose mono- di- or tri-palmitate, can be used as the oil component, although these are not as preferred as the other oils mentioned above. The excipient oil may also be of animal source or any acceptable synthetic substitute therefore.

The amphiphilic phase comprises the emulsifiers and surfactants. Preferred emulsifiers include a phospholipid compound or a mixture of phospholipids. Suitable components include lecithin; MONTANOL-68, EPICURON 120 (Lucas Meyer, Germany) which is a mixture of about 70% of phosphatidylcholine, 12% phosphatidylethanolamine and about 15% other phospholipids; OVOTHIN 160 (Lucas Meyer, Germany) which is a mixture comprising about 60% phosphatidylcholine, 18% phosphatidylethanolamine and 12% other phospholipids; a purified phospholipid mixture; LIPOID E-75 or LIPOID E-80 (Lipoid, Germany) which is a phospholipid mixture comprising about 80% phosphatidylcholine, 8% phosphatidylethanolamine, 3.6% non-polar lipids and about 2% sphingomyelin. Purified egg yolk phospholipids, soybean oil phospholipids or other purified phospholipid mixtures are useful as this component. This listing is representative and not limiting, as other phospholipid materials which are known to those skilled in the art can be used.

The surfactant chosen should preferably be non-ionic to minimize irritation, and one skilled in the art can conduct tests to routinely select specific surfactants for this purpose. Generally, the surfactant is a non-ionic alkylene oxide condensate of an organic compound which contains one or more hydroxyl groups. For example, ethoxylated and/or propoxylated alcohol or ester compounds or mixtures thereof are commonly available and are well known to those skilled in the art. Suitable surfactants include, but are not limited to, TYLOXAPOL; POLOXAMER 4070; POLOXAMER 188; POLYOXYL 40 Stearate; EMULFOR EL-620, POLYSORBATE 80, and POLYSORBATE 20, as well as various compounds sold under the trade name TWEEN (ICI American Inc., Wilmington, Del., U.S.A.), PLURONIC F-68 (trade name of BASF, Ludwigshafen, Germany for a copolymer of polyoxyethylene and polyoxypropylene). At this time, PLURONIC F-68 and the POLOXAMER 188 are preferred. The TYLOXAPOL and TWEEN surfactants are also preferred because they are FDA approved for human use.

The aqueous component will be the continuous phase of the emulsion and may be water, saline or any other suitable aqueous solution which can yield an isotonic and pH controlled preparation.

In addition, the compositions of the invention may also comprise conventional additives such as preservatives and antioxidants. Typical preservatives include Thimerosal, chlorbutanol, and methyl, ethyl, propyl or butyl parabens. The preferred oil phase antioxidant is α-tocopherol or α-tocopherol succinate. The aqueous phase may also include an antioxidant or a chelating agent of a polyamine carboxylic acid such as ethylene diamine tetraacetic acid ("EDTA"), or a pharmaceutically acceptable salt thereof.

The drug, cosmetic, or active ingredient, alone or with the oily excipients, are mixed with a sufficient amount of surfactants and/or dispersing and suspending agents to allow dispersibility within the desired size range in aqueous medium. The surfactant(s) may be any pharmaceutically acceptable one(s) that enable(s) adequate dispersibility and stability of the droplets in aqueous medium, in a form of stable submicron size-range droplets. The drug, with or without oily excipients, is vigorously mixed with an aqueous solution that may contain surfactants, to result in submicron droplets of the drug and excipients. If needed, a high shear mixer and a high pressure homogenizer are employed to achieve the desired droplet size. Sonication is an alternative method to achieve the desired submicron droplet size.

Highly efficient delivery of the submicron droplets to the skin is obtained with a dosage form which is semi-solid. To produce a semi-solid composition, many methods may be applied; addition of gelling agents, such as carbopols and adjusting to a pH, organic thickening agents such as polyvinyl pyrrolidone (PVP) or a hydroxypropyl methyl cellulose (HPMC) polymer, or cetostearyl alcohol and other waxes that may rigidify, solidify or increase the viscosity of the aqueous dispersion to the desired consistency level. Inorganic thickening agents such as fumed silica (AEROSIL or CABOSIL), alumina, clay or other similar colloidal particles can be used to increase the viscosity of the formulation. It is also possible to use oil concentrations on the higher end of the disclosed range to achieve higher viscosity compositions. However, use of greater than 30% oil causes difficulty in achieving the desired droplet size.

Chemical skin penetration enhancers may be incorporated into the formulation to enhance penetration of the active ingredient through the skin. In this regard, DMSO, decyl methyl sulfoxide, N-dodecyl pyrrolidone, decanol, dodecanol, an organic acid such as oleic acid, or the like can be used. Overall pharmacological effects achieved with the combination of chemical enhancers and submicron droplets are greater than for either component used by itself.

This invention provides submicron spheres (or droplets) that are an insoluble assembly of unique entities dispersed in an aqueous phase with the aid of appropriate surfactants or emulsifying agents. The emulsifying agent and surfactant form a protective layer around the droplets thus enabling efficient dispersion and suspension of the oily phase in water. This layer is a monolayer, polar by virtue of the surfactants. The present droplets are neither vesicles nor liposomes since no bilayers resembling the bilayer forming the living cell wall is formed. Micelles may be formed and be present, but may account for only a very small fraction of the surfactants and insoluble matter of the formula and in negligible quantities, usually less than about 1% of the total mass of insoluble matter and surfactants or dispersing agents.

Experiments carried out and measurements by means of photon correlation spectroscopy (Coulter N4MD) and laser diffraction (Coulter LS130) indicated that the droplet size in the compositions of the invention is in the size range of about 0.02 to about 0.5 microns. Preferably, the size range is mainly in the 0.1 to 0.3 micron (i.e., 100 to 300 nm) range.

Depending on the inherent activity of the active ingredient its quantity has to be adjusted for each specific drug.

Compositions according to the invention for topical application to obtain a topical or systemic effect, contain, for example as active ingredient: steroids or non-steroidal anti-inflammatory drugs, antibiotics, antifungals, antivirals, antihistamines, antineoplastics or local anesthetics. Specific examples would include substances such as clotrimazole, bifonazole, tetracycline, miconazole, triamcinolone, amphotericin gentamicin, hydrocortisone, iodoxuridine, diphenhydramine, minoxidil, lidocaine, tetracaine and clindamycin.

For systemic effects, the following categories of drugs are suitable: hypnotics, sedatives, anxiolytics, antidepressants, anticonvulsants, anti-inflammatory drugs, anti-fungals, prostanoids, prostanoid agonists, prostanoid antagonists, analgesics, hormones and vitamins. Specific examples would include lipophilic peptides, barbiturates, benzodiazepines, phenothiazines, cyclosporin, diphenoxylate, physotigmine, tacrine, diclofenac, dexamethasone, prostaglandins, nifedipine, nitroglycerine, atropine, verapamil, fentanyl, lipophilic peptides, ketotifen, phenytoin, miconazole and ketoconazole.

For cosmetic effects, the active ingredient might be for example Vitamin A, Vitamin E, a polyunsaturated fatty acid such as eicosapentanoic acid, retinoids, carotenes and benzoyl peroxide.

Instead of a viscous composition, the droplets of the invention can be topically and transdermally applied by an article which includes the droplets, an active ingredient and a support for retaining the composition thereon. The support would include an adhesive for securing the article to the skin of a subject. A wide variety of active ingredients, including steroids such as estradiol, nicotine or nitroglycerine, can be administered by this article, which would generally be in the form of an occlusive dressing or an adhesive patch.

In the following description, concentrations will be indicated by % which denotes the concentration by weight of the component per 100 units volume of entire composition. All indicated concentrations should be understood as standing each by itself, and not cumulative. It should be appreciated by the artisan, however, that there is some dependency between the concentrations of the components, e.g., higher concentrations of the oil will generally require higher concentrations of the emulsifier and surfactant.

The emulsion used in the compositions of the present invention may comprise about 0.5 to 30% oil, about 0.1 to 10% emulsifier and about 0.05 to 5% surfactants. Generally, increasing the concentration of the non-aqueous phase, i.e., the combined concentration of the oily and the amphiphilic phase, increases viscosity of the composition. In order to obtain a viscous composition, the concentration of the oil could be increased to about 20 to 30%. As noted above, another way to increase the viscosity is to add a pharmaceutically acceptable gelling or thickening agent, such as Carbopol or the like. These viscous compositions are useful as creams or ointments.

Preferred concentrations of the components are as follows: about 5 to 20% oil; about 0.2 to 5% of the emulsifier, with about 0.2 to 1% being particularly preferred; and about 0.2 to 5% for the surfactant, with about 0.2 to 1% being particularly preferred. For a viscous composition, about 0.2 to 15% of the gelling or thickening agent can be included.

The drug or cosmetic agent (the active ingredient) is present in an amount of about 0.05 to 5% by weight of the composition, preferably about 0.1 to 2.5%. Depending upon whether the active ingredient is hydrophilic or hydrophobic, it will be physically present in the oily phase or the aqueous component. Also, the pH of these compositions should be in a range which is suitable for the stability of the active ingredient, but silghtly acidic or as close to neutral as possible for compatibility with the skin.

The invention is illustrated with reference to the above-mentioned examples, which are to be construed in a strictly non-limitative manner.

EXAMPLES

The enhanced topical and transdermal effects of drugs administered in emulsions comprised of submicron size droplets in comparison to standard cream formulations and commercial preparations was established in several test systems. Antiinflammatory agents were tested utilizing the carrageenan induced paw edema in guinea pigs. Tranquilizers were assessed in guinea pigs utilizing behavioral tests indicative of sedation. Local anesthetics were tested in healthy human volunteers on the basis of loss of local sensation following application of various preparations.

The following summarizes the systems used and results obtained with the formulations tested. The following cases are to be construed as examples in a strictly non-limitative manner.

Example 1

A diazepam submicron cream preparation was made as follows: 0.5 g of diazepam are mixed with 9 g of medium chain triglyceride (MCT) oil and 1 g of lecithin until an homogeneous oily phase is achieved. The oily phase is then dispersed into 90 ml of an aqueous phase which includes 2 g of PLURONIC F-68 and 0.1 g of a mixture of methyl and propyl parabens by initial mixing with a magnetic stirrer followed by a high shear mixer (Polytron K3000) for 5 minutes at 20,000 RPM to form an emulsion. Further treatment of the emulsion is conducted in a high pressure homogenizer (APV-Gaulin) at 800 bar for 6 minutes (about 10 cycles) at 45–55° C. Thereafter, the emulsion was cooled to room temperature and the mean droplet size was measured size to be 120 nanometers having a very narrow distribution with practically no droplets above one micron (less than 0.5%) being detected. CARBOPOL is added to a final concentration of 0.3%. Finally, the pH is elevated with sodium hydroxide to 7 and a semi-solid submicron droplet preparation is achieved.

Example 2

Example 1 was repeated using 6 g MCT oil and 3 g oleic acid. The mean droplet size was found to be 150 nanometers.

Example 3

(Comparative) A formulation was made in the same manner as Example 2 but without the procedure to reduce the droplet size. The final droplet size was between 5 and 50 microns.

Example 4

(Comparative) A conventional diazepam cream was prepared as follows: diazepam 0.5 g, MCT oil 9 g, emulsifying wax 9 g, hot water 81 ml. A classical technique was used whereby the wax was melted, the oil and drug were added, and then the hot water was added with vigorous stirring. The mean droplet size of the cream was between 5 and 50 microns.

Example 5

The systemic tranquilizing effect of topically applied diazepam creams of the first four examples were investigated and compared to the systemic administration of diazepam, as follows.

Materials and Methods Guinea pigs, males and females, having a body weight of about 250 g were shaved 24 hours before application of the creams. The following formulations were applied: (a) diazepam 0.5%—small drops (Example 1); (b) diazepam 0.5%—small drops with oleic acid (Example 2); (c) diazepam 0.5%—large drops with oleic acid (Example 3); (d) diazepam 0.5% in a conventional cream of large droplet size (Example 4). Five grams of each preparation was applied on the shaved area, i.e., about 20 $cm_2$ of each guinea pig.

Commercially available parenteral preparations were also used as controls, as follows: (e) diazepam 5 mg/ml (vials of 2 ml), 10 mg/kg administered intramuscularly, and (f) the same preparation administered subcutaneously (10 mg/kg).

Clinical appearance, following application or injection, was checked and recorded. The onset and termination times of the effects were recorded.

Three basic behavioral tests, indicating level of sedation, were used (a) Righting reflex: animals are positioned on their back and the time that is required to return to normal position was recorded. Three levels of sedation are scored: low (score 1)—animal returns immediately to normal position; moderate (score 2)—up to 30 seconds are needed to return to normal position; severe-deep (score 3)—more than 30 seconds are needed to regain normal position.

(b) Step test: animals are positioned on a 5 cm high step, with the forelegs on the step. The time interval for changing this position was measured for each animal. The same course of time that was used for scoring of righting reflex was used here.

(c) Animals were positioned on their hind legs, their forelegs put on the top of their cage (20 cm high). The time interval for changing this position was measured for each animal. The same scoring methodology as above was used here.

(d) A total aggregate score for each animal was calculated to show the state of sedation for this study.

The results are shown in Table 1. It was found that topically applied diazepam is very effective when delivered in submicron droplets. A systemic-like effect may be achieved with this preparation, but the same dose in large droplet formulation was not effective. Also, the inclusion of oleic acid in the formulation reduces the time for onset of activity and duration.

TABLE 1

Efficacy of Different Topical and Systemic Diazepam Formulations in Guinea Pigs

| Treatment | No. of Animals | Score | Time of Activity (min) |
| --- | --- | --- | --- |
| Diazepam, i.m., 10 mg/kg | 4 | 39.0 | 15–120 |
| Diazepam, s.c., 10 mg/kg | 4 | 52.8 | 15–120 |
| Diazepam 0.5% cream (5 g) submicron drops | 5 | 47.5 | 45–240 |
| Diazepam 0.5% cream (5 g) submicron drops with oleic acid | 6 | 43.7 | 30–120 |
| Diazepam 0.5% cream (5 g) large drops with oleic acid | 5 | 3.0 | — |
| Classical diazepam 0.5% cream (5 g) | 5 | — | — |

Example 6

Example 1 was repeated using TWEEN-80 instead of PLURONIC F-68. The mean droplet size was 170 nanometers and an enhanced tranquilizing effect substantially equivalent to that of Example 1 was detected.

Example 7

Example 1 was repeated using EMULFOR EL-620 instead of PLURONIC F-68. The mean droplet size was found to be 100 nanometers and the activity was comparable to that of Example 1.

Example 8

Example 1 was again repeated except that the formulation contained 20 g MCT oil. The mean droplet size was found to be 210 nanometers, but the activity was significantly increased in comparison to Comparative Example 4 and was as good as that of Example 1.

Example 9

Example 1 was repeated except that 20 g MCT oil and 1 g diazepam were used. The mean droplet size was 250 nanometers and the preparation exhibited increased activity compared to that of Comparative Example 4 which was at least as good as that of Example 1.

Example 10

Example 1 was again repeated but 1 g oleic acid was included. The mean droplet size was 100 nanometers and the composition was found to be as active as that of Example 1.

Example 11

Example 1 was repeated using TWEEN-65 instead of lecithin. The mean droplet size was found to be 250 nanometers and the formulation was much more active (a score of 35) than that of Example 4.

Example 12

Example 1 was repeated using MONTANOL-68 instead of lecithin. The mean droplet size was found to be 300 nanometers and the formulation was much more active (a score of 30) than that of Example 4.

Example 13

Example 1 was repeated using soybean oil instead of MCT oil. The mean droplet size was found to be 180 nanometers and the formulation was as active as that of Example 1 (a score of 45).

Example 14

Example 1 was repeated with the addition of α-tocopherol as an antioxidant. The mean droplet size was found to be 100 nanometers and the formulation was as active as that of Example 1. This formulation was also found to be suitable for administering oxidation sensitive drugs such as nifedipine.

Examples 15–16

Example 1 was again repeated but 2 g of AEROSIL silica and hydroxypropyl cellulose, respectively, were included instead of CARBOPOL, and the pH was adjusted to 5.5. The mean droplet size for each example was found to be 180 nanometers and the compositions were found to be as active as that of Example 1.

Example 17

An indomethacin submicron cream preparation was made a follows: indomethacin 0.5 g, MCT oil 17 g, lecithin 0.8 g, EMULFOR EL-620 1.6 g, CARBOPOL 1.7 g and water 78 ml. The procedure of Example 1 was followed to obtain a mean droplet size of 130 nanometers.

Example 18

(Comparative) A conventional, large droplet size indomethacin cream was prepared as follows: indomethacin 0.5 g, MCT oil 15 g, emulsifying wax 9 g, water 75 ml. The composition was prepared as in Example 2. The mean droplet size was found to be between 5–50 µm.

Example 19

The topical anti-inflammatory effect of topically-applied indomethacin creams of Examples 17–18 were investigated and compared for their anti-inflammatory effect versus systemic administration.

Animals and Materials
   (a) Guinea pigs (250 g).
   (b) Indomethacin 0.5% in submicron cream (Example 17).
   (c) Indomethacin 0.5% in conventional cream (Example 18).
   (d) Indomethacin 0.5% in solution.

Study Procedure
   (a) All animals received an injection of 0.1 ml carrageenan 0.1% into the hind paw. Measurements were taken from the area of injection and followed for up to 5 hours.
   (b) The above creams were administered at carrageenan administration site and the solution of indomethacin was administered intramuscularly 15 minutes prior to carrageenan administration.
   (c) The circumference of the paw was again measured and the change in size was compared for the different treatments. The volume changes were measured by a plethysmometer (Ugo, Basel).

The results presented in Table 2 demonstrate that a local application of indomethacin in submicron droplet cream was the most effective in reducing the edema caused by the carrageenan injection, and was more effective than large droplets of indomethacin cream or the same dose administered intramuscularly.

TABLE 2

Performance of Different Indomethacin Formulations in Paw Edema Model in Guinea Pigs

| Treatment | No. of Animals | Average change of circumference, percent Hours after carrageenan injection | | | | |
|---|---|---|---|---|---|---|
| | | 1 | 2 | 3 | 4 | 5 |
| Control (Carrageenan) | 4 | 17 | 32 | 61 | 80 | 83 |
| Indomethacin 0.5%, in cream small droplets | 4 | 0 | 7.3 | 24 | 32 | 36 |
| Indomethacin in cream, Large droplets | 4 | 16 | 55 | 67 | 47 | 39 |
| Indomethacin 10 mg/kg i.m. in solution | 4 | 19 | 22 | 25 | 36 | 33 |

Example 20

A lidocaine submicron cream preparation was made as follows: lidocaine 4 g, MCT oil 6.5 mg, lecithin 0.8 g, EMULFOR EL-620 1.5 g, water 78 ml and CARBOPOL 1.7 g. Again, the procedures were the same as in Examples 1 and 17. The mean droplet size was found to be 160 nm.

Example 21

(Comparative) A conventional, large droplet size lidocaine cream was prepared as per Example 3 except with lidocaine 4 g, MCT oil 5.5 g, emulsifying wax 8 g, petroleum 14 g, water 69 ml. The mean droplet size was greater than 50 microns.

Example 22

A small droplet size eutectic local anesthetic was prepared as follows. 2.2 g lidocaine, 2.2 g tetracaine, 2 g PLURONIC F-68, 89 g water, and carbopol 4.5 g. The preparation procedure was as per Example 1, the pH was adjusted to 7.5 and the mean droplet size was found to be 250 nanometers.

Example 23

(Comparative) A conventional, large droplet size eutectic local anesthetic was prepared as follows. The same formulation as in Example 22 was prepared but without the procedure to reduce the droplet size. The final droplet size was found to be between 20–100 µm.

Example 24

The local anesthetic effect of topically applied lidocaine creams of Examples 20–23 were investigated and compared. Each preparation was applied to the forearm of 4 male human volunteers and the degree of local anesthesia with time was monitored. A gentle touch was made with a sharp needle and the sensitivity of an adjacent (untreated) area was compared to the application site to estimate the effectiveness of the tested preparation. The experiment was blind for the volunteers. The sensitivity at the site of application was given a score of intensity of 1 to 4 and an average dosage form performance was calculated. The results are shown in Table 3.

TABLE 3

Average Score (Effectiveness) of Small vs. Large Droplet Size Lidocaine Creams

| Droplets | Small | Large |
|---|---|---|
| Example # | 19 | 20 |
| Drug Conc., % | 4 | 4 |
| Droplet size, um | 0.25 | 10–50 |
| Delay, hours | 0.5 | 1 |
| Duration, hours | 4.5 | 3 |
| Effectiveness (Average Score) | 28 | 17 |

These data show that lidocaine alone in oleaginous base or in regular cream of emulsifying wax (i.e., one having a droplet size of greater than 50 microns), was not effective as local anesthetic. However, the small droplet size preparation of lidocaine provided local anesthesia and performed better than larger droplet size which was very poor. Moreover, the small droplet size eutectic mixture performed better than the same formulation but with large droplet size, as shown in Table 4.

TABLE 4

Average Score (Effectiveness) of Small vs. Large Droplet Size Eutectic Local Anesthetic Mixture Creams

| Droplets | Small | Large |
|---|---|---|
| Example # | 21 | 22 |
| Drug Conc., % | 4.4 | 4.4 |
| Droplet size, µm | 0.295 | 20–100 |
| Delay, hours | 0.3 | 0.5 |
| Duration, hours | 6 | 4.5 |
| Effectiveness (Average Score) | 58 | 40 |

Example 25

A diclofenac submicron cream was prepared as follows: Oil phase—diclofenac diethylammonium 12.2 g, MCT oil 170 g, LIPOID E-80 30 g, α-tocopherol succinate 0.4 g; Aqueous phase—EDTA disodium salt 1 g, EMULFOR EL-620 25 g, glycerol 17.5 g, preservatives (methyl and propyl parabens) 0.5 g, reverse osmosis purified water to 1000 g.

The composition was prepared as follows. The emulsion was prepared by combining the oil and aqueous phases together with a magnetic stirrer for 5 minutes, followed by a high-speed, high-shear mixer (Polytron K3000) for 5 minutes at 3000 RPM. The emulsion which was obtained was treated by a high pressure homogenizer (APV-Gaulin) at 800 bar (6 minutes, about 10 cycles) at 45–55° C. After homogenization, the emulsion was allowed to cool to room temperature, the particle size distribution was determined and the emulsion was then filtered through a 0.45 micron pore size filter (Unimodal) size after 8 cycles/800 bar is 120±30 nm, with the dust before filtration being in the range of 2–4%.

The cream formulation was prepared as follows: To 1000 g of the emulsion, 50 g of 10% CARBOPOL 940, which was pre-swollen in purified water, was added and mixed thoroughly with the Polytron K3000 device at 5–10,000 RPM for 2–3 minutes. Pure triethanolamine was added dropwise with mixing to adjust the pH to 6–6.5. A final mixing with the Polytron K3000 device at the same conditions produces a cream which contains 1.16% Diclofenac DEA (which is equal to a 1% solution of sodium diclofenac). After pH, viscosity and drug content testing, the cream is packed into aluminum tubes.

Example 26

Figure 1:
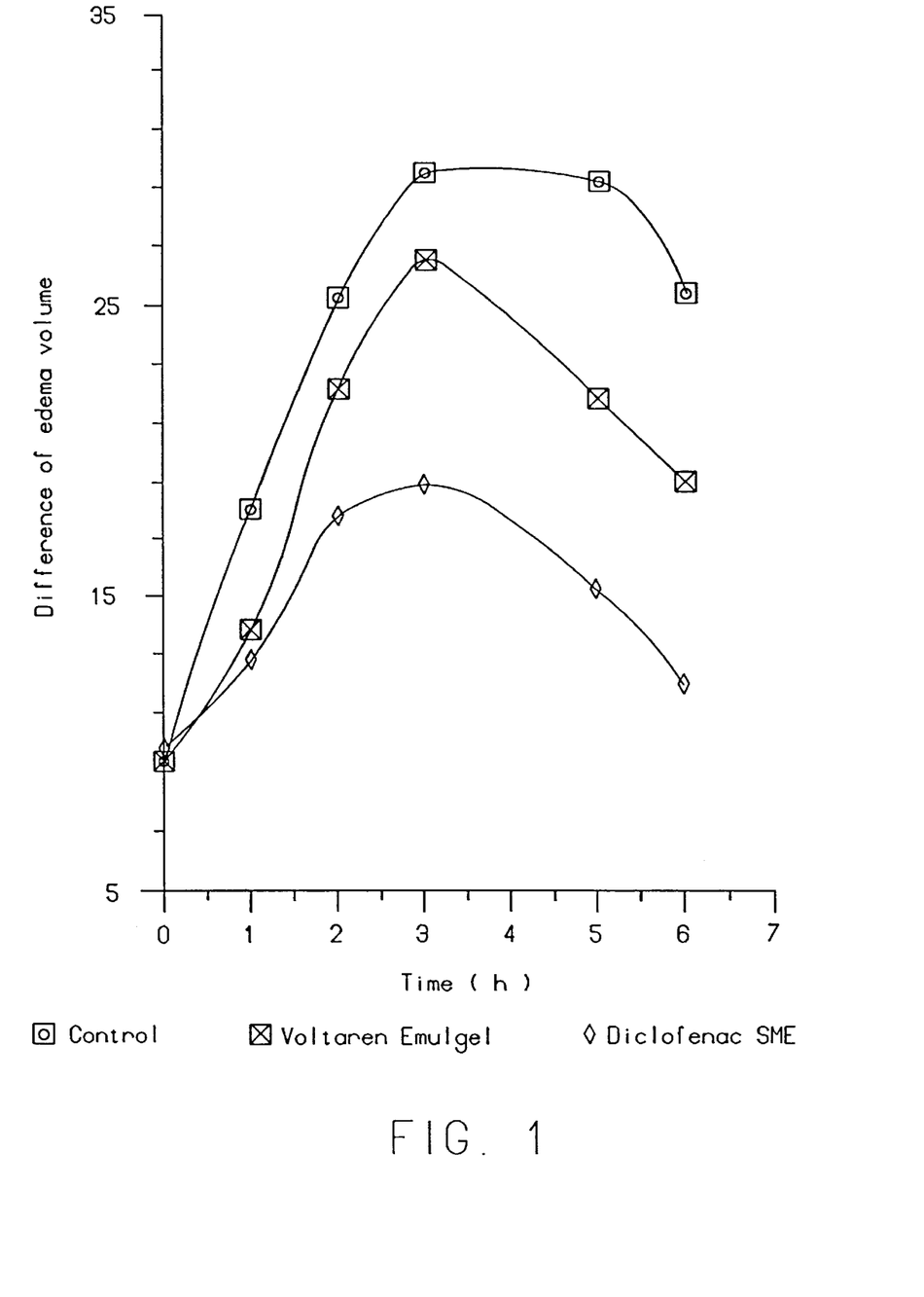
FIG. 1 is a graphical illustration of the effects of edema over time during treatment with various diclofenac creams.
Figure 2:
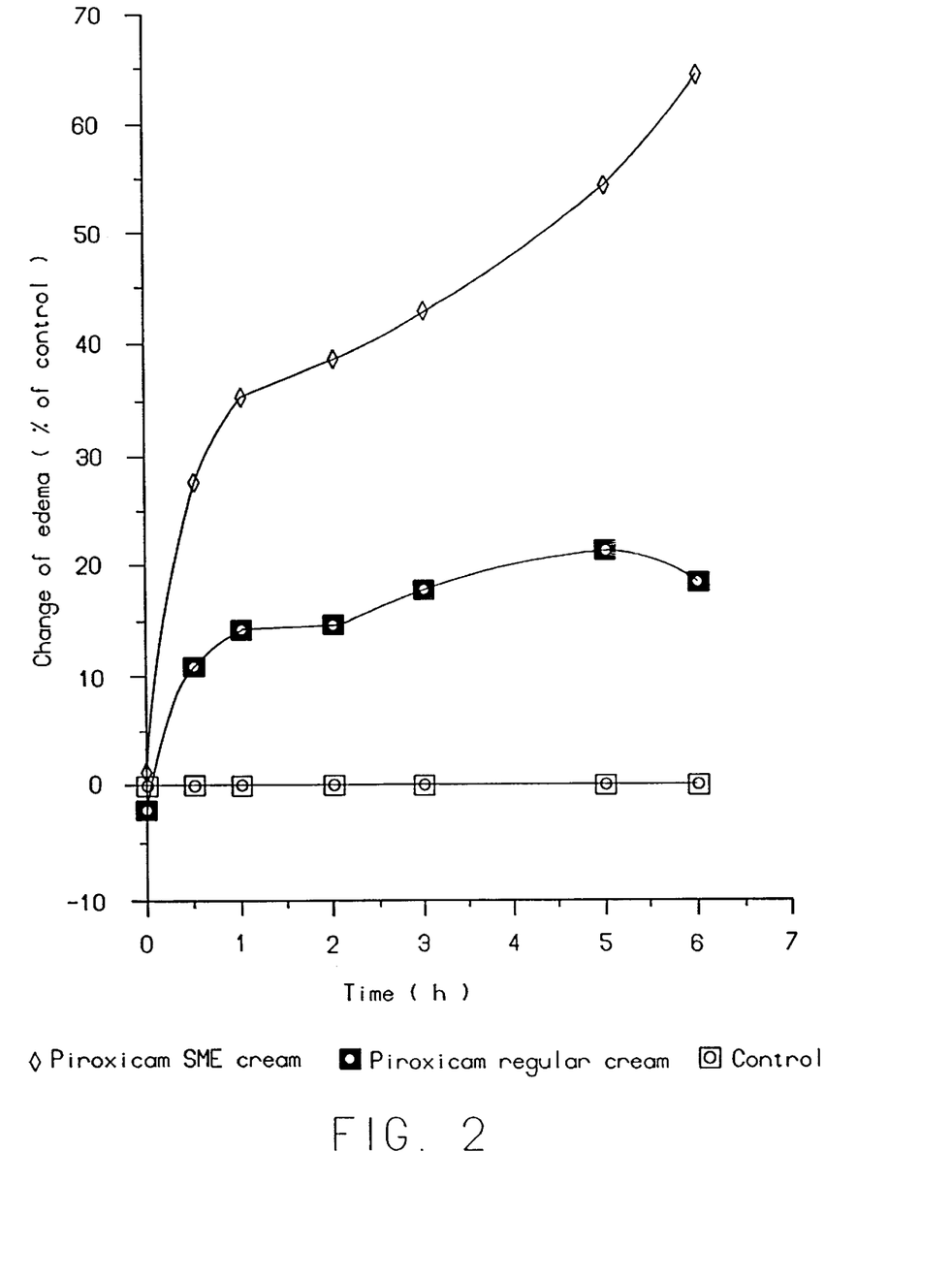
FIG. 2 is a graphical illustration of the relative difference over time during treatment with various diclofenac creams.

A topical edema treatment by diclofenac in different droplet size formulations was evaluated. A formulation containing submicron droplets of diclofenac (Example 25) was compared to standard preparation using the carrageenan paw edema model (guinea pigs). Carrageenan (0–1 ml of 0.1% solution) was injected into hind paw (at time=o). Start size of edema at time zero was taken as 100% level. Surface of edema was treated immediately after carrageenan injection by test preparations:
  a) 1.16% diclofenac diethylammonia (equivalent to 1.0% Diclofenac sodium) in submicron emulsion (90–150 nm droplets) (Example 25).
  b) VOLTAREN EMULGEL (Ciba-Geigy)—as a reference composition with known activity. c) 1.16% diclofenac diethylammonia in large droplets (5–10 µm). Changes in volume were made using a plethysmometer (Ugo, Basel), and the results are shown in FIG. 1.

Example 27

A piroxicam small droplet cream was prepared from the following components: piroxicam 0.25 g, MCT oil 9.5 g, lecithin 0.5 g, Tween-80 0.5 g, water 38.4 g, carbopol 0.2 g, triethylamine 0.2 g. The composition was prepared as in Example 1. The mean droplet size was found to be 127 nm.

Example 28

(Comparative) A conventional piroxicam (large droplet) cream was prepared as follows: piroxicam 0.178 g, MCT oil 5 g, cetosteryl alcohol 2.7 g, sodium dodecylsulfate 0.3 g, water 27 g. After melting together the cetostearyl alcohol with sodium dodecylsulfate, the MCT oil was added. Piroxicam was mixed with ready hot oil phase, and then 27 ml of boiling water was added and mixed thoroughly. After cooling to room temperature, the cream was obtained.

Example 29

Figure 3:
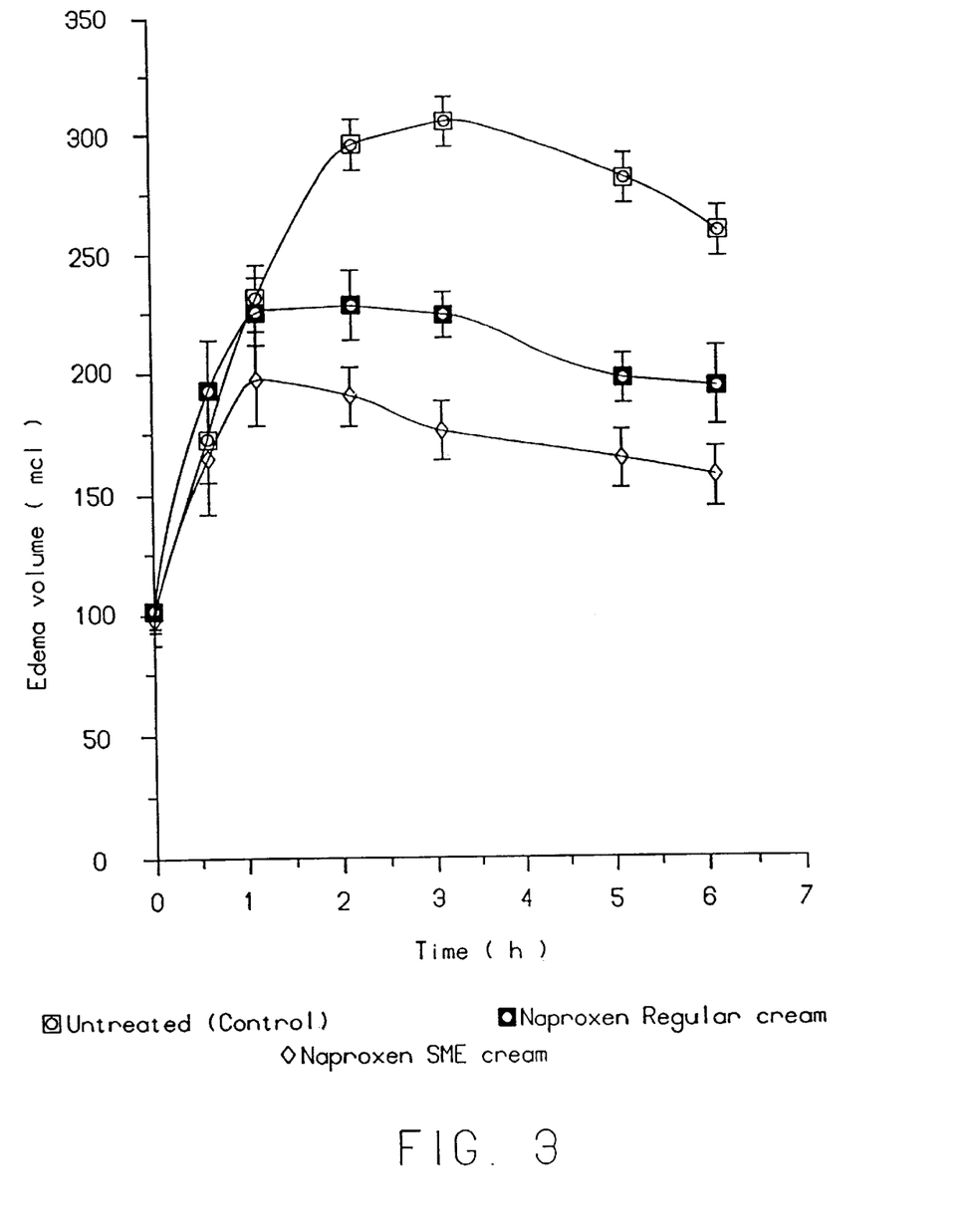
FIG. 3 is a graphical illustration of the effects of edema over time during treatment with various naproxen creams.

A topical edema treatment by piroxicam in different emulsion formulations was studied. The submicron droplets of piroxicam (Example 27) was compared to standard cream (Example 28) using the carrageenan paw edema model (guinea pigs) of Example 26. As shown in FIG. 3, piroxicam in the cream of Example 27 demonstrates relatively low antiinflammatory activity, while the formulation of Example 26 was found to be much more effective.

Example 30

A topical naproxen submicron cream was prepared from the following components: naproxen 1 g; Miglyol 810 17 g; LIPOID E-80 3 g; α-tocopherol succinate 0.04 g; EMULFOR EL-620 2.5 g; glycerol 1.75 g; EDTA disodium dihydrate 0.1 g; CARBOPOL 940 0.5 g; triethanolamine 0.5 g; and pure water to 100 g. The naproxen, MIGLYOL 810, LIPOID E-80 and α-tocopherol succinate were mixed together at 45° C. until completely dissolved to form an oil phase. The EMULFOR, glycerol and EDTA were dissolved in water and mixed thoroughly with the oil phase in a high shear mixer (Polytron K3000) for 5 minutes at about 20,000 RPM to form an emulsion. Further treatment of the emulsion is conducted in a high pressure homogenizer (APV-Gaulin) at 800 bar for 8 cycles to a droplet size of about 100–150 nm. After filtration through a 0.45 micron filter, CARBOPOL in the form of a preswollen gel (10% in water) was added and mixed in the Polytron device for 2 minutes at 5000 RPM. The triethanolamine was added to a final pH of 5.5–6.5 and the formulation was mixed in the Polytron device until a homogeneous cream was obtained.

Example 31

A topical edema treatment by naproxen in different formulations was studied. A submicron droplet cream of naproxen (Example 30) was compared to a standard cream using the carrageenan paw edema model (guinea pigs) of Examples 26 and 29 for the following formulations:
  a) Naproxen in a submicron emulsion (100–150 nm droplets as per Example 30) applied topically.
  b) Naproxen in a conventional cream (droplets larger than 20 microns) applied topically.

The results are illustrated in FIG. 3

What is claimed is:

1. A composition for topical application of pharmaceuticals or cosmetics comprising submicron size droplets comprising about 0.5 to 30% of a first component of an oily liquid, about 0.1 to 10% of a second component of an emulsifier, about 0.05 to 5% of a surfactant, and an active ingredient of at least one lipophilic peptide in the amount of 0.5 to 5%, said droplets having a mean droplet size in the range of 0.05 to 0.5 µm, wherein said composition provides an enhanced topical and/or transdermal systemic effect compared to the same compositions which have larger droplets.

2. A composition for enhanced topical and/or transdermal delivery of pharmaceuticals comprising submicron droplets having a mean droplet size of 0.05 to 0.3 microns dispersed in an aqueous medium containing one or more pharmaceutically-acceptable surfactants, wherein said droplets are comprised of an effective amount of a water-insoluble drug mixed with one or more medium chain triglyceride oils having a chain length of eight to twelve carbons.

3. The composition of claim 2 wherein the mean droplet size is between about 0.1 and 0.3 µm.

4. The composition of claim 2 wherein the surfactant is a non-ionic alkylene oxide condensate of an organic compound which contains one or more hydroxyl groups.

5. The composition of claim 4 wherein the surfactant is an ethoxylated alcohol or ester compound.

6. The composition of claim 5 wherein the non-ionic surfactant is present in an amount of about 0.2 to 5%.

7. The composition of claim 2 which further comprises an active ingredient in an amount of 0.5 to 5%.

8. The composition of claim 2, further comprising an aqueous component which forms the continuous phase of an oil-in-water emulsion, with the droplets forming the oil phase of the emulsion.

9. The composition of claim 2, further comprising a dispersion enhancer in an amount sufficient to promote the homogeneity of the composition.

10. The composition of claim 2 further comprising a viscosity enhancing agent in an amount sufficient to impart a semi-solid form to the composition.

11. The composition of claim 10, wherein the viscosity enhancing agent is a physiologically acceptable organic or inorganic thickening agent.

12. The composition of claim 11, wherein the viscosity enhancing agent is an organic thickening agent comprising a high molecular weight organic compound or an inorganic thickening agent comprising colloidal particles.

13. The composition of claim 2 further comprising a skin penetration enhancer in an amount sufficient to enhance the penetration of the composition through skin after the composition is topically applied thereto.

14. The composition of claim 13, wherein the skin penetration enhancer is DMSO, decyl methyl sulfoxide, N-dodecyl pyrrolidone, decanol, dodecanol, or an organic acid.

15. The composition of claim 7, wherein the active ingredient is at least one steroid, non-steroidal antiinflammatory drug, antibiotic, tranquilizer, sedative, antihistaminic, antifungal, antibacterial, antiviral, disinfectant, antipsoriasis, immunosuppressant, vasodilator or vasoconstrictor agent or a local anesthetic.

16. The composition of claim 15 where the active ingredient is clotrimazole, bifonazole, tetracycline, miconazole, triamcinolone, amphotericin B, gentamicin, hydrocortisone, iodoxuridine, diphenhydramine, minoxidil, lidocaine, tetracaine and clindamycin.

17. A method for achieving local anesthesia or analgesia, or for providing general analgesia which comprises formulating a composition comprising submicron size droplets comprising about 0.5 to 30% of a first component of an oily liquid, about 0.1 to 10% of a second component of an emulsifier, about 0.05 to 5% of a surfactant, and an active ingredient in the amount of 0.5 to 5%, said droplets having a mean droplet size in the range of 0.05 to 0.5 µm, wherein said composition provides an enhanced topical and/or transdermal systemic effect compared to the same compositions which have larger droplets and topically applying the composition to a subject.

* * * * *